United States Patent [19]
Altman et al.

[11] Patent Number: 5,845,396
[45] Date of Patent: Dec. 8, 1998

[54] CO-RADIAL, MULTI-POLAR COILED CABLE LEAD AND METHOD FOR MAKING THE SAME

[75] Inventors: Peter A. Altman, San Francisco; Drew A. Hoffmann, Los Gatos, both of Calif.

[73] Assignee: Pacesetter, Inc., Sunnyvale, Calif.

[21] Appl. No.: 767,912

[22] Filed: Dec. 17, 1996

[51] Int. Cl.$^6$ .................................................. H01R 43/28
[52] U.S. Cl. .............................. 29/885; 29/882; 29/883; 607/116
[58] Field of Search .............................. 29/828, 876, 883, 29/885; 607/116, 122, 119, 123; 600/372, 373; 174/128.1, 128.2, 105 R, 113 R, 108

[56] References Cited

U.S. PATENT DOCUMENTS

| | | | |
|---|---|---|---|
| 3,308,523 | 3/1967 | Ivester et al. | 264/294 |
| 3,649,744 | 3/1972 | Coleman | 174/113 R X |
| 4,640,983 | 2/1987 | Comte | 174/119 |
| 4,683,349 | 7/1987 | Takebe | 174/69 |
| 4,840,186 | 6/1989 | Leckholm et al. | 607/116 |
| 4,988,833 | 1/1991 | Lai | 174/69 |
| 5,182,785 | 1/1993 | Savegh et al. | 385/128 |
| 5,366,493 | 11/1994 | Scheiner et al. | 607/116 |
| 5,476,495 | 12/1995 | Kordis et al. | 607/122 |
| 5,483,022 | 1/1996 | Mar | 174/128.1 |

FOREIGN PATENT DOCUMENTS 1146228  5/1983  Canada .............. H01B 7/00

OTHER PUBLICATIONS

"Fatigue Performance of Stimulating Electrodes" Comte, et al, *Biomedizinische Technik,* Band 28, Erganzungsband, May 1983, 2 pgs.

"Long–Term Performance of Endocardial Pacing Leads", Helguera, et al., *PACE,* vol. 17, Jan. 1994, pp. 56–64.

"A Study of the Fatigue Properties of Small Diameter Wires used in Intramuscular Electrodes", Scheiner,et al., *Journal of Biomedical Materials Research,* vol.25,1991,pp. 589–608.

*Primary Examiner*—Peter Vo
*Assistant Examiner*—Rick Kiltae Chang
*Attorney, Agent, or Firm*—Steven M. Mitchell

[57] ABSTRACT

A method for making a co-radial, multi-polar coiled cable lead. The method includes the steps of attaching a first end of a coated cable to a mandrel using a first end fixture. The coated cable comprises one or more cable strands, where each strand is made from one or more filaments. After the first end of the cable is attached to the mandrel, the cable is wound around the mandrel to form a coiled cable. A second end of the coiled cable is then attached to the mandrel using a second end fixture to retain the coiled cable under tension. Second stage processing is then performed on the coiled cable so that the end fixtures may be subsequently removed from the coiled cable without the coiled cable unwinding. After the second stage processing is complete, the coiled cable can be used in the manufacture of an implantable lead.

21 Claims, 13 Drawing Sheets

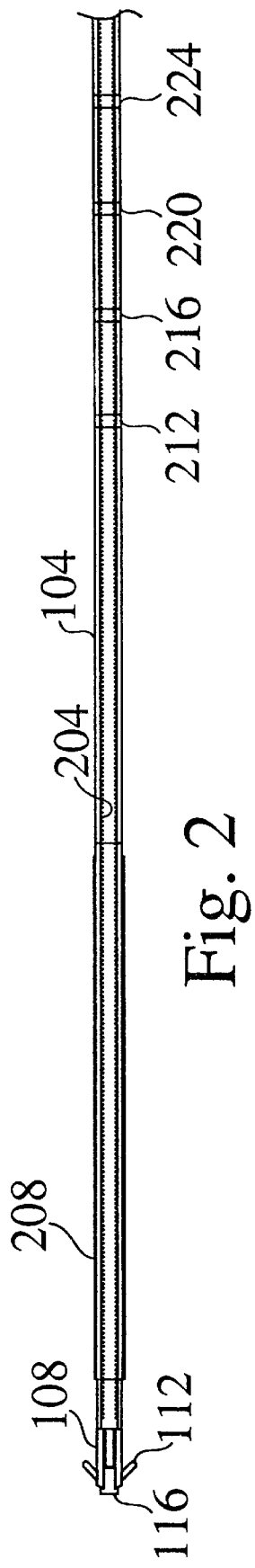
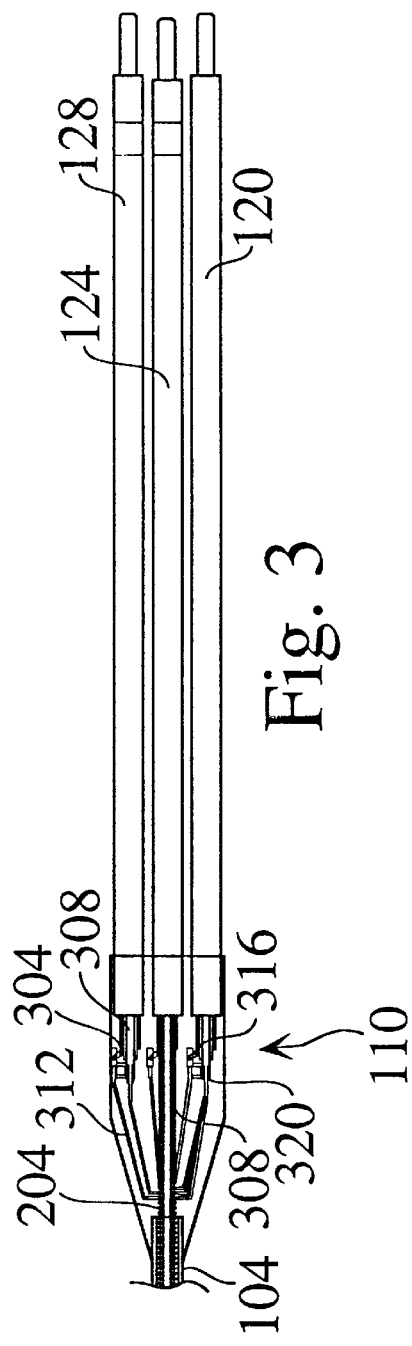
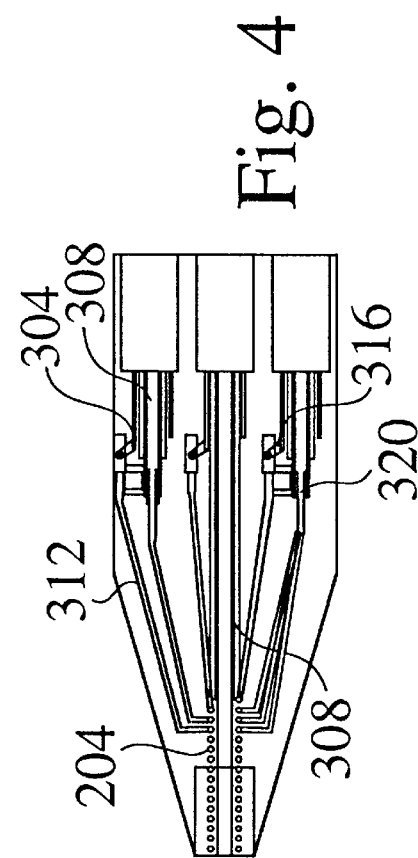
Fig. 2
Fig. 3
Fig. 4

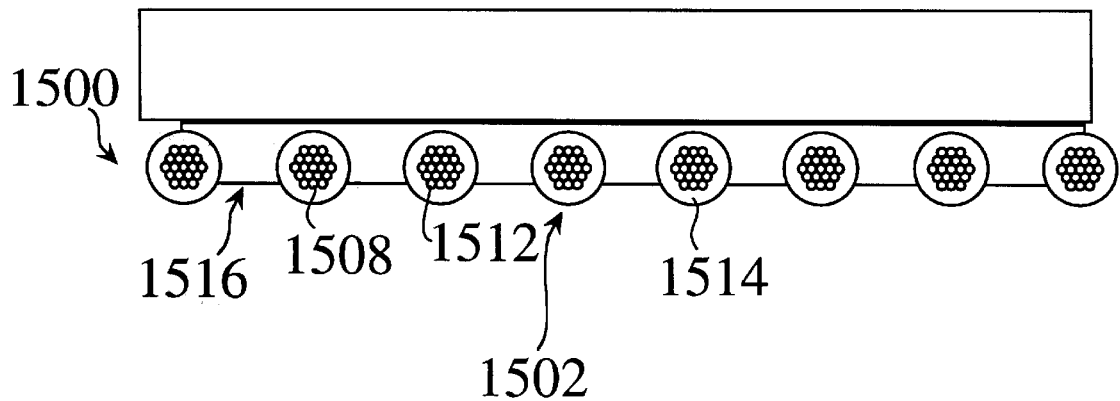
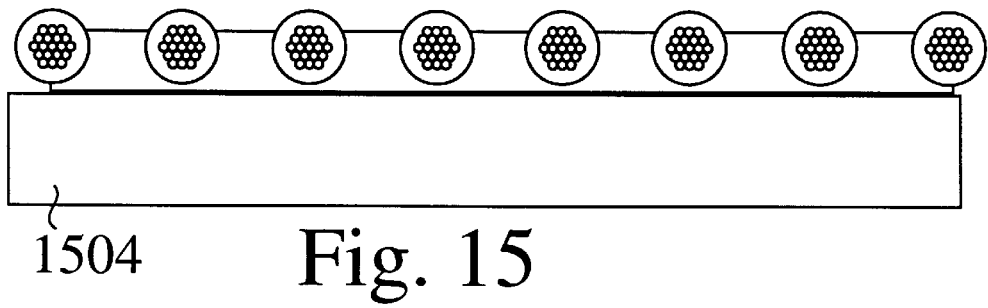
Fig. 15
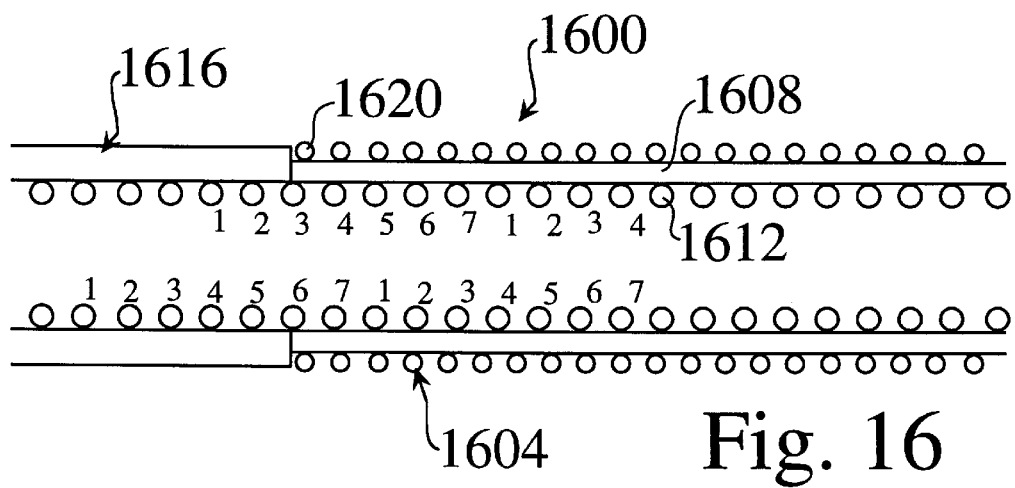
Fig. 16

CO-RADIAL, MULTI-POLAR COILED CABLE LEAD AND METHOD FOR MAKING THE SAME

BACKGROUND OF THE INVENTION

1. Field of the Invention

The present invention relates to implantable conductors for biological stimulation. In particular, the present invention relates to implantable conductors for delivery of electrical pulses to the heart and sensing electrical activity of the heart and methods for making the same.

2. Related Art

Defibrillator and pacemaker leads are electrical conductors implanted through the venous system of the human body to deliver electrical therapy to and sense electrical activity of the heart. Cardiac motion requires that these leads withstand hundreds of millions of bending cycles over their useful life. Although a study of lead performance by M. E. Helguera, in an article entitled, "Long term performance of endocardial pacing leads", PACE, 17, 56–64, 1994, shows that ten years after implantation, the incidence of verified lead fracture is less than 3%, the criticality of the lead component and the large number of implants, greater than 250,000 per year, require high reliability of each lead implanted.

To maximize fatigue life, lead design has been directed towards minimizing the stresses experienced by the different conductive structures used to manufacture the lead. For example, coiling a straight wire conductor has been shown to decrease the stresses on the wire in bending, and has resulted in the use of low stress, coiled wires in many of the leads implanted today. Previous work in assessing the fatigue characteristics of implantable conductors has focused on empirical fatigue studies of different conductor materials and geometries. In a study by P. Comte et al., documented in an article entitled, "Fatigue performance of stimulating electrodes", Biomedizinische Technik, Band 28, Erganzungsband, 1983, the disclosure of which is incorporated herein by reference, rotary bending tests were performed to explore the effects of coil geometry and material on the fatigue of coils in bending. These tests show that decreased filarity, wire diameter, increased coil diameter, increased radius of the loop test, and decreased spacing between windings of the coil wires each correspond to increased fatigue resistance.

The stress in a straight wire introduced by bending decreases in proportion to decreases in the diameter of the wire. Thus, A. Scheiner et al. in an article entitled, "A study of the fatigue properties of small diameter wires used in intramuscular electrodes," J. Biomed. Mater. Res, 25, 589–608, 1991, the disclosure of which is incorporated herein by reference, teaches the use of cable structures composed of very small straight wires to decrease stress and increase fatigue life of the lead. Rotary loop tests performed on small diameter intramuscular electrode wires and cables, and assessment of fatigue failure using microscopic examination, show that fatigue life for a cable increases as the diameter of the wire within the cable decreases. Thus, use of the smallest, most reliably manufactured wire for forming cabled conductors will maximize fatigue life.

In forming a conventional coiled solid wire for use in an implantable lead, the wire is wound around a spindle, or mandrel, under tension. The stresses introduced to the solid wire during winding are large enough to plastically deform the wire material so that the resulting coil maintains a shape substantially close to that of the coil under tension, even after tension on the wire is removed.

In the case of a coiled, multi-filar cable structure, the stresses introduced in winding a cable, formed of smaller wires, about a mandrel are generally insufficient to introduce substantial plastic deformation of the cable wires. Thus, after tension is removed from a coiled cable, the coil begins to unwind.

The unwinding of the coiled cable structure is problematic when trying to use this structure to manufacture implantable leads. It would be preferable to use a coiled cable to manufacture implantable leads, because a coiled cable will provide lower stresses, better flexure and fatigue life, and axial symmetry for a variety of lead designs. Further, reduced stresses of coiled cable lead designs coupled with co-radial placement of different conductors will allow smaller leads to be made. Still further, a co-radial coiled cable configuration will provide a more flexible lead structure. Thus, means are needed to manufacture coiled cable structures which would prevent them from unwinding during manufacture of implantable leads.

SUMMARY OF THE INVENTION

The present invention is a co-radial, multi-polar, coiled cable lead and method of making the same. The coiled cable lead of the present invention is designed to be used as a pacing/sensing or defibrillation/sensing lead for the heart. Thin filaments of conductive material are combined to form multi-filar strands. One or more strands are used to form a cable. Two or more cables are formed into coils which are used as conductors in the lead to deliver electrical energy to or sense electrical activity of the heart.

The method for manufacturing the co-radial, multi-polar, coiled cable lead includes the steps of drawing thin conductor filaments and forming these filaments into strands. One or more strands are then used to form a cable. Each cable is coated with a fluoropolymer, polyimide or polyurethane coating and placed in a winder apparatus.

A first end of each cable is attached to a mandrel in the winder. For example, each cable could be mechanically attached to the mandrel by a wire or tape that is wound over the first end of each cable to secure them to the mandrel. Specialized clamps could also be used to prevent the tension of the winding from being released from the structure. Alternatively, the cables could be attached to the mandrel by inserting the first end of each cable into a hole that has been drilled into the mandrel. In a further alternative, the cables may be attached to the mandrel by welding.

After attaching the cables to the mandrel, the cables are wound around the mandrel. After winding, a second end of each cable is attached to the mandrel. The second end of each cable could be attached to the mandrel using any of the means described above. Further, the second end of each cable could be press fit into a notch that has been made in the mandrel. The ends of the filaments are then trimmed and the mandrel and coil cables are removed from the winder apparatus. Finally, a second stage process is performed on the cables so that the cables may be removed from the mandrel without unwinding.

This second stage process includes one or more of the following processes: silicone dispersion coating the coiled cables, inserting the coiled cables into a preformed biocompatible tube, thermal relaxation of the cable coating after winding, applying tape around the coiled cables, and/or compression molding a tube around the coiled cables.

One method for performing second stage processing is to form a tube around the coiled cables by silicone dispersion coating. This process allows a tube to be built up around the coiled cables without removal of the fixtures on either end. In this method, the coiled cables are dipped in uncured silicone rubber dispersed in a solvent. After each dipping, a layer of tubing accumulates on the coiled cables. Once the layer(s) have been cured, a coating around the coiled cables results.

If the coiled cables are close wound, that is, having no space between windings, the dispersion coating process will result in a jacket of silicone forming over the coiled cables which is very similar to tubing. If the coiled cables are wound with a space between the windings, the dispersion coating process will result in the coiled cables being partially embedded in a silicone wall. Because the mandrel and end fixtures remain in place during the coating process, the inner surface of the coiled cables will be free of silicone dispersion coating. Once the process forms a coating having a thickness sufficient to resist the residual stresses in the coiled cables, the fixtures can be removed from the ends of the coiled cables, and the silicone-coated, coiled cables can be removed from the mandrel.

In an alternate method used for second stage processing, the dispersion coated, coiled cables can be placed in a preformed, biocompatible tube. This tube provides an additional mechanism for resisting the residual stresses in the coiled cables.

A supplemental process, known as thermal relaxation, can be used to reduce the residual stresses in the coating of each cable. This process involves heating the cables to just below the melting point of the coating. With the standard thin wall coatings used on cables, thermal relaxation of the coating is not sufficient to prevent unwinding of the coiled cables. However, thermal relaxation does reduce the residual stresses that the tubing or dispersion coating will have to overcome to prevent unwinding of the coiled cables. Temperatures used for thermal relaxation are much lower than those that would affect the wire structures, and should not be high enough to melt the cable coating. The cables are then dispersion coated to form a silicone tube around the coiled cables as described above. A preformed tube can also be placed around the coated, coiled cables to further resist any residual stresses in the coiled cables.

Tape materials may also be used to prevent unwinding of the coiled cables. In particular, tape made from polyurethane, polytetrafluoroethylene (PTFE), commonly referred to as TEFLON®, expanded polytetrafluoroethylene (ePTFE), also known as GORTEX®, polyimides, or other polymers may be wrapped over the coiled cables to create restraining hoop stresses around the coiled cables. After tape has been wrapped around the coiled cables, the end fixtures can be removed. Alternatively, a biocompatible thread may be wrapped around the cables to prevent unwinding. The taped, coiled cables may also be either dispersion coated or inserted into a biocompatible tube, or both, to provide a redundant mechanism for resisting the residual stresses in the coiled cables.

Another method which could be used to prevent the coiled cables from unwinding is welding. In particular, the ends of each of the coiled cables could be welded to the mandrel using resistance welding. If using coated cables, the coating on the ends of the cables must be removed while the cables are under tension and prior to welding. After the structure is welded to the mandrel, the end fixtures may be removed. Then, the ends of the coiled cables are trimmed and the weld points are deburred. Because the weld points do not increase the cross-sectional area of the coiled cables as much as the end fixtures, the entire coiled cable structure may be inserted directly into a biocompatible tube. The coiled cables could also be dispersion coated after welding but before being inserted into a tube. Such external structures will maintain the shape of the coiled cables once the welded ends are removed. Once formed, and removed from the mandrel, the coiled cable structure may be used as an independent element in lead design.

Another method used to form a tube around the coiled cables to prevent unwinding is by compression molding. This process is similar to silicone dispersion coating in that the coiled cable structure is overmolded, so that the fixtures on either end of the coiled cables do not have to be removed before molding. In this process, a compression mold is configured to accommodate the ends of the coiled cables having the fixtures.

In molding a long conductor such as a lead, it may be difficult to create a perfectly concentric structure. Thus, different techniques should be used to optimize concentricity of the resulting tube, such as the use of force plates to prepack the mold, the use of a two stage molding processes, and the like. These techniques are well known to those skilled in the relevant art. Once the outer jacket is molded over the coiled cable structure, the fixtures are removed from the cables, and the encased coiled cables may be removed from the mandrel.

The lower stresses provided by using a coiled cable structure to manufacture an implantable lead will result in higher fatigue resistance and increased flexibility. The reduced stress of the coiled cable lead designs will allow leads to be made with more independent conductors, and at smaller diameters. Thus, the coiled cable structure of the present invention results in a more flexible conductor than the conventional lead design.

The axial symmetry of the coiled cable leads will result in uniform stresses regardless of the direction of flexure. Thus, the symmetry increases the reliability of fatigue tests in bending and compression, because there is little concern for the orientation of the structure. Such symmetry provides uniform handling characteristics for the implanting physician because the bending rigidity of the lead will be the same in all directions.

In contrast, a multi-polar conductor formed of parallel cables or parallel coils will not be axi-symmetric and will have different bending characteristics depending upon which direction the structure is bent. These different characteristics will affect testing, handling, and even reliability.

BRIEF DESCRIPTION OF THE FIGURES

The foregoing and other features and advantages of the invention will be apparent from the following, more particular description of a preferred embodiment of the invention, as illustrated in the accompanying drawings.

FIG. 2 shows a partial cross-sectional view of a lead body and a lead tip portion of the lead of the present invention.

FIG. 3 shows a partial cross-sectional view of a trifurcation and connectors of the lead of the present invention.

FIG. 4 shows a more detailed view of the trifurcation of the present invention.

FIG. 15 shows a sectional view of a space-wound, coiled, co-radial cable of the present invention which has been dispersion coated and inserted into a silicone tube.

FIG. 16 shows a sectional view of a coiled, co-radial cable of the present invention inserted inside a lead body tubing and a defibrillation electrode coil subassembly.

DETAILED DESCRIPTION OF THE PREFERRED EMBODIMENTS

A preferred embodiment of the present invention is now described with reference to the figures where like reference numbers indicate identical or fimctionally similar elements. Also in the figures, the left most digit of each reference number corresponds to the figure in which the reference number is first used. While specific configurations and arrangements are discussed, it should be understood that this is done for illustrative purposes only. A person skilled in the relevant art will recognize that other configurations and arrangements can be used without departing from the spirit and scope of the invention. It will be apparent to a person skilled in the relevant art that this invention can also be employed in a variety of other devices and applications.

Figure 1:
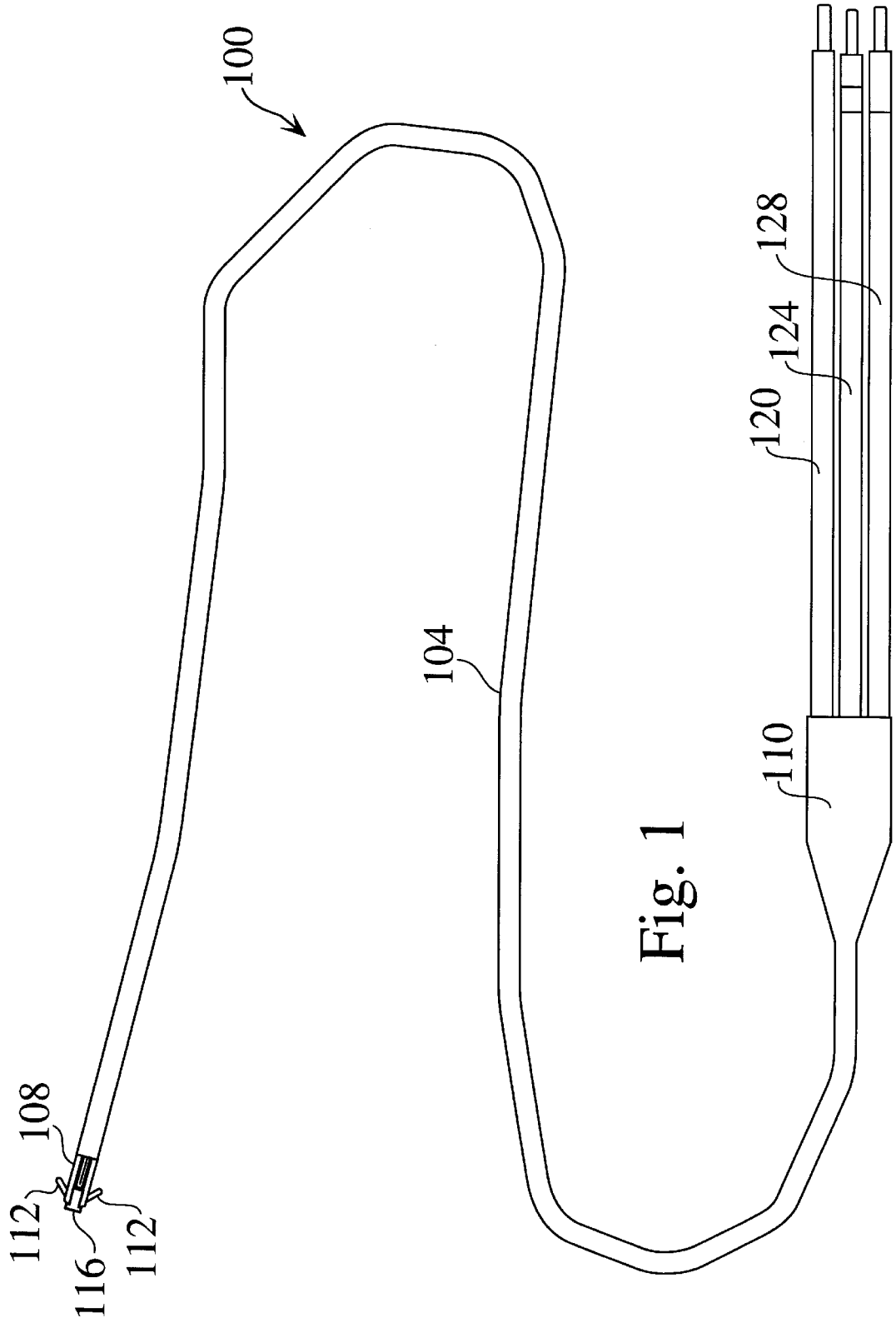
FIG. 1 shows a lead of the present invention.

FIG. 1 shows a lead 100 of the present invention. Lead 100 includes a lead body 104, having a lead tip portion 108 on one end and a trifurcation 110 on the other end thereof. The coiled cables of the present invention, discussed in further detail below, are disposed within lead body 104.

Lead tip portion 108 includes a conventional passive fixation device 112, for example, tines commonly used for fixation of the lead to the patient's heart wall. Further, lead tip portion 108 includes a pacing tip 116 for providing electrical pulses to the heart. In one embodiment, trifurcation 110 includes a defibrillation connector leg 120 and bipolar connector legs 124 and 128. In the preferred embodiment, a DF-1 defibrillation connector is used at the end of connector leg 120 and IS-I bipolar connectors are used at the ends of connector legs 124 and 128. Trifurcation 110 will be described in further detail below with respect to FIGS. 3 and 4.

FIG. 2 shows a partial cross-sectional view of lead body 104 and lead tip portion 108 of lead 100. In FIG. 2, a multi-conductor coil formed from a co-radial, coiled cable structure 204 of the present invention is disposed inside lead body 104. A defibrillation electrode 208 is disposed on lead body 104 near lead tip portion 108. Ring sensing electrodes 212, 216, 220 and 224 are also disposed on lead body 104, as shown in FIG. 2.

FIGS. 3 and 4 show partial cross-sectional views of trifurcation 110 of the present invention. Trifurcation 110 houses electrical connections between defibrillation connector leg 120 and bipolar connector legs 124 and 128 and coiled cable structure 204. Connector legs 124 and 128 each have an outer coil 304 and an inner coil 308. Connector leg 120 has a single inner coil 308. Outer coils 304 and inner coils 308 extend outwardly from connector legs 120, 124 and 128, and extend into trifurcation 110.

Outer coils 304 are connected to cables 312 of the splayed coiled cable 204 via a connector 316. Inner coils 308 of defibrillation connector leg 120 and bipolar connector leg 128 are connected to cables 312 of the splayed coiled cable 204 via a connector 320. The ends of cable 312 thus electrically connect coiled cable 204 to outer coils 304 and inner coils 308 so that electrical energy is passed from the ends of connector legs 120, 124 and 128 to coiled cable structure 204.

Inner coil 308 of bipolar connector leg 124 extends outwardly through coiled cable structure 204 and into lead body 104. Inner coil 308 of bipolar connector leg 124 may act as a stylet guide. Inner coil 308 of connector legs 124 and 128 each are inner coils of a co-axial coil pair, and inner coil 308 of connector leg 124 meets with a co-axial coil of lead body 104. In an alternate embodiment, lead body 104 does not include a central co-axial coil. Further, coiled cable structure 204 of the present invention, as described in further detail with respect to FIGS. 6–16, provides a conductor with a long fatigue life and good flexibility in a relatively small lead body.

Figure 5:
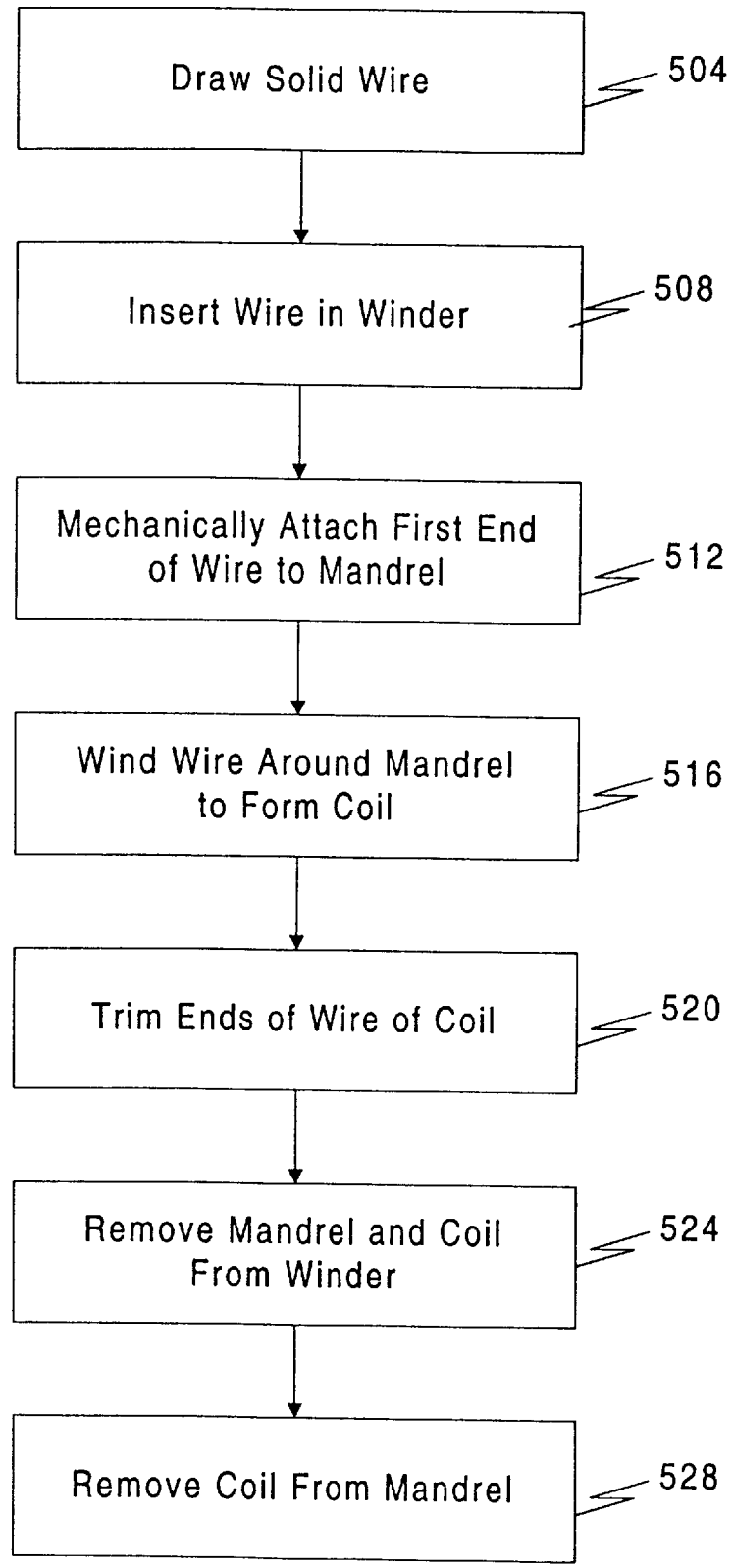
FIG. 5 is a flowchart showing a conventional method for winding coils from solid wires.

The flowchart of FIG. 5 shows a conventional method for winding coils from solid wires. In a step 504, a solid wire is drawn. This single wire is electrically conductive and typically has a diameter between approximately 0.004 and 0.010 inches. The wire is then inserted into a winder apparatus, as shown in a step 508. Generally, the wire is disposed on a spool. The winder apparatus is configured to receive the spool so that wire can be fed from the spool through the winder apparatus. A first end of the wire is attached to a mandrel, as shown in a step 512. The mandrel is a core, usually made of a metal, around which the wire is wound. In a step 516, the wire is then wound around the mandrel to form a coil. After the coil is wound, the wires at both ends of the coil are trimmed, as shown in a step 520. The mandrel and coil are then removed from the winder, as shown in a step 524. Finally, the coil is removed from the mandrel, as described in a step 528. Stresses introduced during winding of the coil cause plastic deformation of the solid wire. Thus, after removal of the mandrel, the wire remains coiled. The coil can then be inserted into a tube that is made of a biocompatible material to form an implantable conductor.

Figure 6:
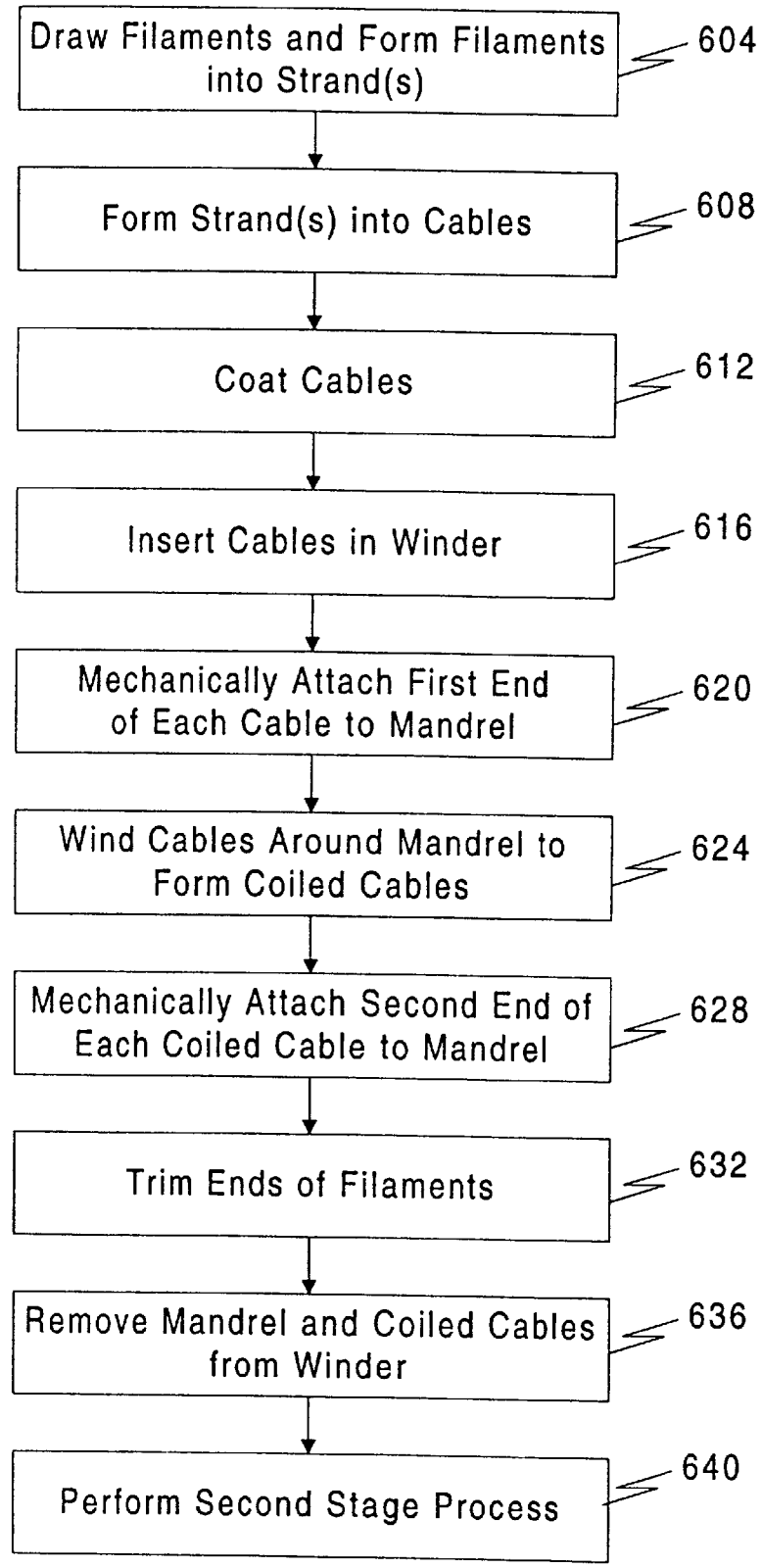
FIG. 6 is a flowchart showing a method for winding co-radial, coiled cable structures according to the present invention.

FIG. 6 shows a method for winding a co-radial, coiled cable structure according to the present invention. In a step 604, filaments are drawn and formed into a strand. Filaments are fine wires made from an electrically conductive material, and which are preferably made with the smallest possible diameter that can be reliably made using known techniques. In the preferred embodiment, each filament is between approximately 0.0005 and 0.0015 inches.

In the preferred embodiment, the filaments are made from either a solid nickel-cobalt alloy, commonly referred to as MP35N wire, a platinum-iridium (Pt/Ir) wire, drawn filled tube (DFT) made from MP35N wire having a silver core, or drawn brazed strand (DBS) wire made from 316LVM stainless steel over a silver core, available from Fort Wayne Metals. Many other wire types may also be used to form the filaments, such as DFT formed with a platinum jacket and a silver core. Other wire types will be apparent to one skilled in the art of lead design.

Thus, a strand is formed from a number of filaments, using known techniques. One or more strands are then used to form a cable in a step 608. Two or more of these cables can be used to form the coiled cable structure of the present invention, as shown in FIG. 16.

The cables of the present invention are then coated with a polymer insulating material in a step 612. For example, the cables could be coated with ethylene-tetrafluoroethylene (ETFE), polytetrafluoroethylene (PTFE), perfluoroalkoxy (PFA), polyurethane (PU), polyimide (PE) or fluorinated ethylene-propylene (FEP). These coatings electrically insulate the multi-polar cables from each other during winding.

The coated cables are then inserted into a winder apparatus, as shown in a step 616. A first end of each cable is attached to a mandrel, as shown in a step 620. The first end of each cable can be attached to the mandrel using a variety of fixation means. For example, a restraining wire could be tightly wound around the cables and mandrel to attach one to the other. Alternatively, a clamping mechanism could be clamped around the cables and mandrel. Further, the cables and mandrel could be attached using an adhesive, screw, welding or other fastening means.

In a step 624, the cables are wound around the mandrel to form coiled cables. However, because substantial plastic deformation of the thin filaments in the strands of the cables does not occur during winding, the coiled cables cannot be removed from the mandrel at this stage of the process without causing them to unwind. It is noted that if sufficient tension was applied to the cables during winding, severe plastic deformation of the filaments may occur to prevent unwinding of the coiled cables. However, application of the amount of force necessary to deform the filaments would likely result in fracture of the filaments, damage to the insulative coating on the cables, build up of inherent residual stresses in the insulative coating on the cables, and other flaws to the integrity of the structural properties of the resulting conductor. Thus, application of these types of forces to the cables during winding is not recommended.

In a step 628, a second end of each coiled cable is attached to the mandrel to retain the cables in a coiled form. Any one of the fixation means discussed above can be used in step 628. The ends of the filaments are then trimmed in a step 632. The mandrel and coiled cables are removed from the winder apparatus, in a step 636. As shown in a step 640, a second stage processing step must be performed on the coiled cables to prevent them from unwinding when they are removed from the mandrel. Several embodiments of the second stage processing step are described in further detail below with respect to FIGS. 7–12.

Figure 7:
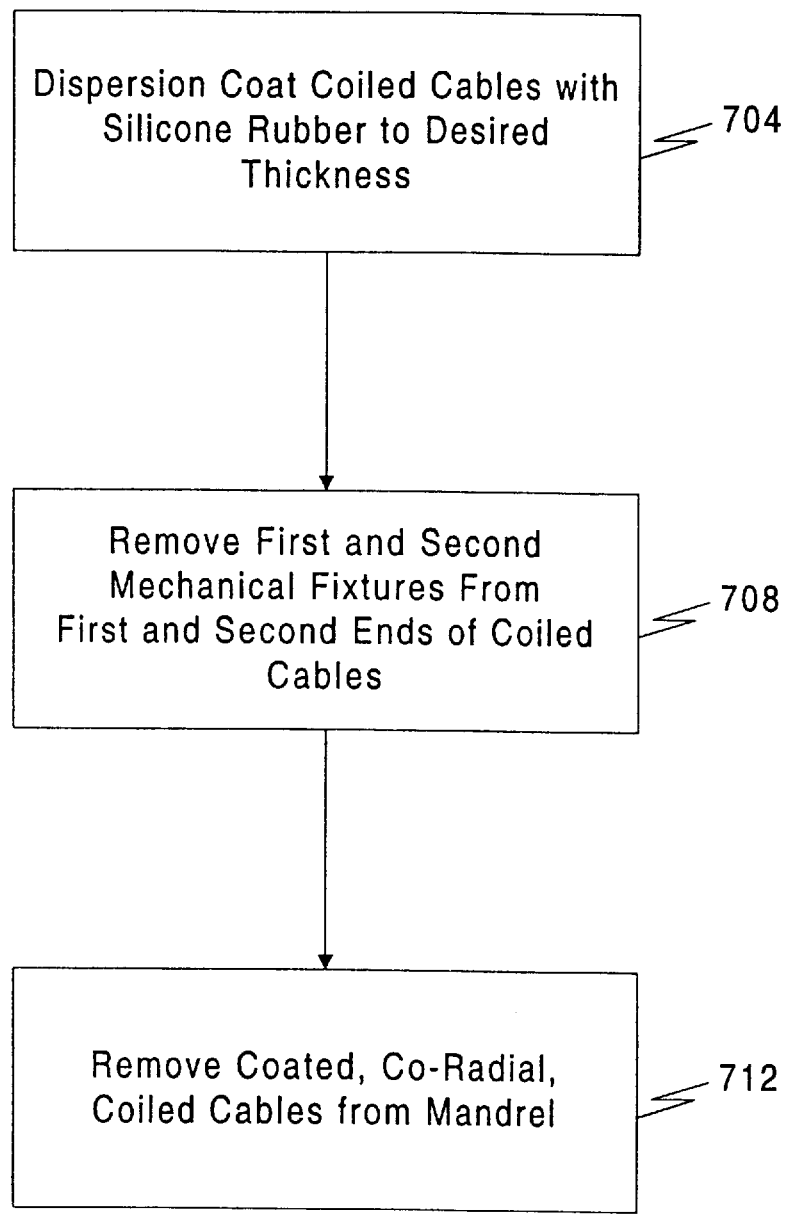
FIG. 7 is a flowchart showing a first embodiment for performing a second stage process for winding coiled cable structures according to the present invention.

FIG. 7 shows a first embodiment of second stage processing step 640 of the present invention in greater detail. In this embodiment, the fixed coiled cables are dispersion coated to form a tube around the coiled cables, as shown in a step 704. The tube has a sufficient thickness to overcome the residual stresses in the coiled cables. Thus, the dispersion coating process allows a tube to be built up around the coiled cables without removal of the fixtures on either end of the cables. Ideally, a preformed tube would be slid over the coiled cables. However, the end fixtures on either end of each of the coiled cables increase the cross-sectional area of the coiled cables so that a tube cannot be slid over the coiled cables at this stage in the manufacturing process. Thus, dispersion coating is one option for forming a tube around the coiled cables without removal of the end fixtures.

The dispersion coating must be thick enough to remain mechanically stable throughout the lead's useful life, to resist the residual stresses in the coiled cables. For example, in a 7×7 cable, that is, a cable having seven strands, each strand being made up of seven small filaments, shown in detail in FIG. 14, the dispersion coating is approximately 0.015 inches. In a 1×19 cable, formed of nineteen strands, each strand made up of one small filament, shown in detail in FIG. 13, the dispersion coating may be thinner, because the residual stresses in the 1×19 cable are less. Although the dispersion coating is capable of overcoming the residual stresses in the coiled cables, it is preferable to minimize the residual stresses in the coiled cables by making the coiled cables as small as possible.

If the cables are designed to ultimately be placed inside a preformed tube, then the dispersion coating can be thinner, because the dispersion coating has to resist the residual stresses in the coiled cables only long enough to detach the coiled cables from the mandrel and place the coiled cables within the tube. This embodiment is discussed in further detail below with respect to FIG. 8.

In the dispersion coating process, the coiled cables are dipped repeatedly in uncured silicone rubber dissolved in a solvent. After each dipping, a layer of tubing accumulates as the solvent evaporates. Although each layer may be cured after the solvent evaporates, in the preferred embodiment, all layers are cured simultaneously. Depending on the type of material used for the dispersion coating, the layers may be cured by several different methods, commonly known to those skilled in the relevant art. For example, if room temperature vulcanizing dispersion is used, (e.g., the solvent is alcohol), the layers do not require higher temperatures for cross-linking. Other types of dispersion coating may require the dispersion coating to be thermally cured by heating the structure in an oven or the like. The thickness of the outer coating provides mechanical stability in vivo.

If the windings of the coiled cables to be coated are close wound, such that there is no space between the adjacent windings of the coiled cables, the dispersion coating will result in a jacket of silicone over the coiled cables which is very similar to tubing. If the windings of the coiled cables are space wound, such that there is a space between the windings in the coiled cables, the dispersion coating will result in a jacket that is similar to embedding the coils in a silicone wall. In a space-wound coiled cable structure, the dispersion coating may be used to maintain the spacing between the windings. Further, in the case of a space-wound coiled cable structure, the silicone rubber fills the spaces between the coil windings and prevents them from sliding relative to each other.

The mandrel and end fixtures remain in place during the dispersion coating process so that the inner surface of the coiled cables are free of silicone dispersion. In the preferred embodiment, the coiled cable structure is dipped into the dispersant inside a vacuum chamber to reduce bubble formation in the dispersion coating. Further, the coiled cables are outgassed between dips in a vacuum environment.

Once a coating forms on the coiled cables to provide a tube having a thickness sufficient to resist the residual stresses in the coiled cables, the fixtures can be removed from the ends of the coiled cables, as shown in a step 708. Then, in a step 712, the dispersion-coated, coiled cables are removed from the mandrel.

Figure 8:
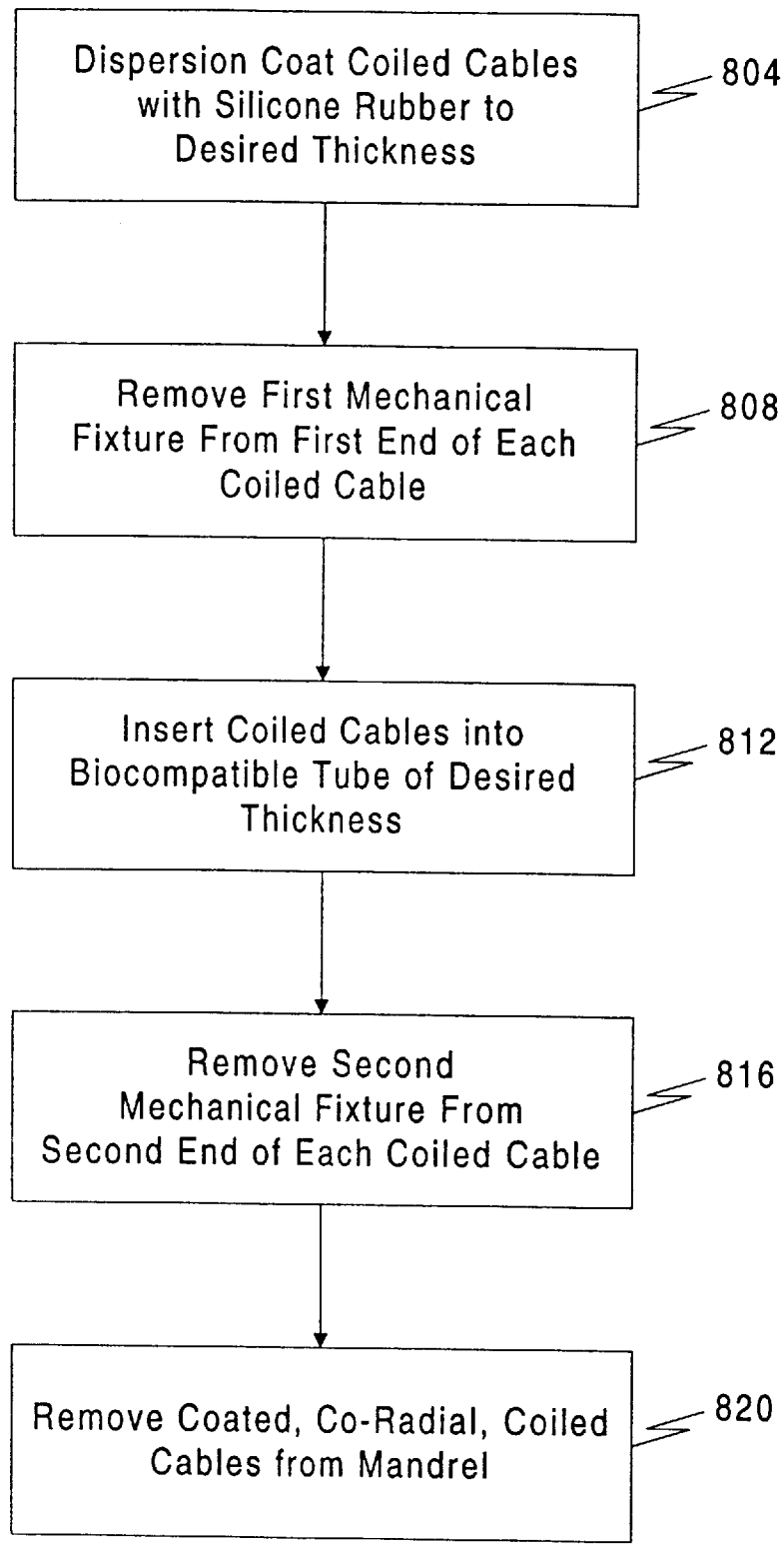
FIG. 8 is a flowchart showing a second embodiment for performing a second stage process for winding coiled cable structures according to the present invention.

FIG. 8 shows a second embodiment of second stage process step 640 of the present invention. In this method, the fixed coiled cables are dispersion coated, in a step 804, using the same process described above with respect to FIG. 7. Dispersion coating step 804 produces a coating having a sufficient thickness to temporarily overcome the residual stresses in the coiled cables until the structure can be inserted into a preformed, biocompatible tube. After the dispersion coating process is complete and the coating is fully cured, the first end fixture is removed from the first end of each of the coiled cables, as shown in a step 808. The "free" end of the coiled cables are then inserted into a biocompatible tube having a desired thickness, as shown in a step 812. This tube is made from a biocompatible material, such as silicone or polyurethane. The tube must be thick enough to withstand the residual stresses in the coiled cables to prevent the cables from unwinding. It is preferred that a tube is placed over the dispersion-coated, coiled cables to prevent unwinding of the coiled cables, rather than relying solely on a layer of dispersion coating to prevent unwinding. The dispersion coating process inherently presents problems with bubble formation and uniformity that are not present in a preformed tube.

After the coiled cables have been placed in the tube, the second end fixture is removed from the second end of each of the coiled cables in a step 816. Once the fixtures have been removed, the coiled cables and tube can be used in the manufacture of an implantable lead, and eventually be removed from the mandrel, as shown in step 820.

Figure 9:
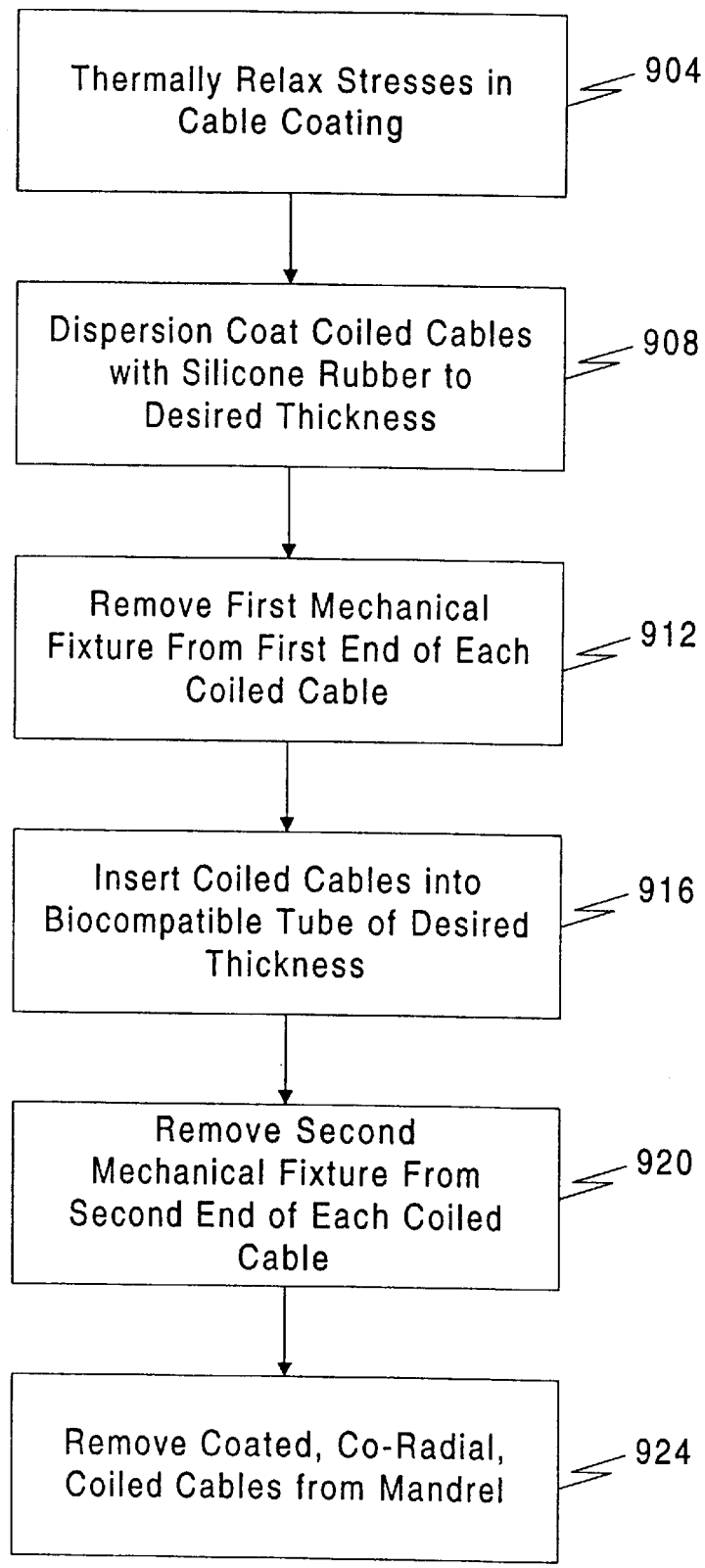
FIG. 9 is a flowchart showing a third embodiment for performing a second stage process for winding coiled cable structures according to the present invention.

FIG. 9 shows a third embodiment of second stage process step 640 of the present invention. This embodiment includes the same steps as in the second embodiment, described with respect to FIG. 8, except that the third embodiment includes an additional step at the beginning of the process. In a step 904, the stresses in the polymer coating on the cables are thermally relaxed by placing the cables in an oven on low heat near, but below, the melting point of the coating. This step reduces residual stresses in the cable coating, which have a tendency to force the coating to spring-back into its original configuration. Further, thermal relaxation of the cable coating assists in resisting the unwinding of the cables, because it will take more residual stresses from the conductive filaments to cause the relaxed coating to deform from its new relaxed coil shape.

In the preferred embodiment, the initial fluoropolymer or polyurethane coating is very thin and would not be sufficient to overcome the residual stresses in the coiled cables. Embodiments could be created where this initial coating is much thicker, increasing the effect of step 904 on the residual stresses in the coiled cables.

After the initial coating of the cables have been thermally relaxed, the coiled cables are then dispersion coated with silicone rubber in a step 908. After the dispersion coating has fully cured, the first end fixture from the first end of each of the coiled cables is removed in a step 912. Then, the first end of each of the coiled cables is inserted into a biocompatible tube of a thickness to resist the residual stresses of the coiled cables.

After the coiled cables are placed in the tube, the second end fixture is removed from the second end of each of the coiled cables, in a step 920. At this point, the coiled cables are contained within the tube and cannot unwind. Thus, in a step 924, the coiled cables can be used to manufacture an implantable lead, and eventually can be removed from the mandrel.

Figure 10:
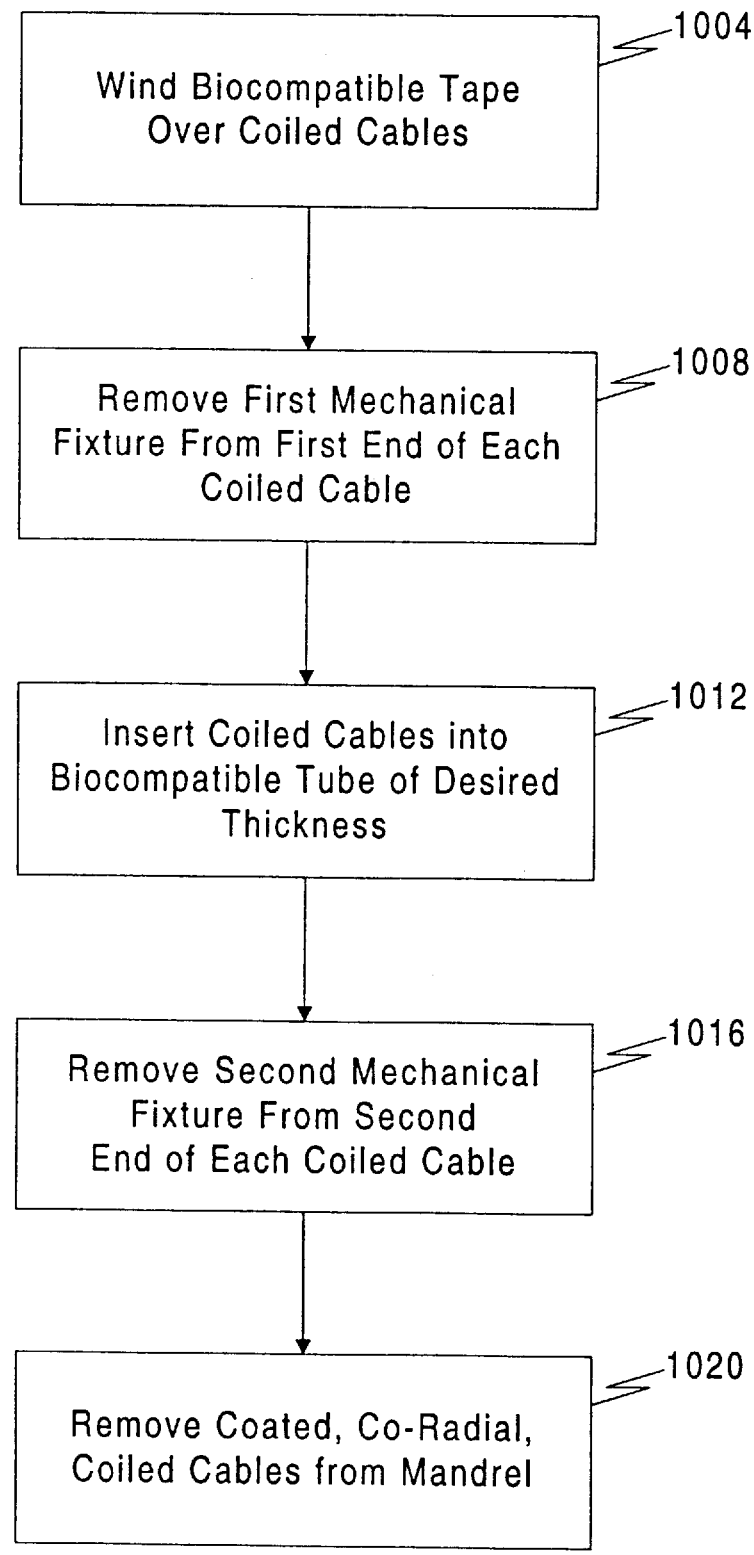
FIG. 10 is a flowchart showing a fourth embodiment for performing a second stage process for winding coiled cable structures according to the present invention.

FIG. 10 shows a fourth embodiment of second stage process step 640 of the present invention. This method is identical to the process disclosed with respect to FIG. 7, except that a new preliminary step 1004 is added. In step 1004, a biocompatible tape or thread is wound over the coiled cables prior to removing the first end fixture from the first end of each of the coiled cables. Biocompatible tape or thread materials made from PTFE, ePTFE, polyester, polyimides or polyurethane can be used. The tape or thread can be wrapped around the coiled cables by hand, after removing the mandrel from the winder. Alternatively, tape or thread could be wound around the coiled cables before step 636, while the cables are still in the winder. In this case, the winder apparatus is used to apply the tape or thread to the coiled cables. The tape material may be porous, as in the preferred embodiment, and a nonporous jacket can be placed over it after winding.

After the tape or thread has been wrapped, the end fixture on the first end of each of the coiled cables can be removed, as shown in step 1008, enabling the coiled cables to be inserted into a tube, as shown in a step 1012. The end fixture on the second end of each of the coiled cables is then removed, as shown in a step 1016. Alternatively, both end fixtures can be removed from the ends of the coiled cables before step 1012 so that the tube can be slid over the coiled cables from either end. In a further alternate embodiment, the taped coiled cables are dispersion coated, instead of, or in addition to, being inserted into a tube. The coiled cables are then removed from the mandrel, as shown in a step 1020.

The tape will maintain the cables in a coiled position. However, creep in the tape may cause it to deform over time. Thus, the residual stresses in the coiled cables could eventually be applied to the outer tubing. The creep effects of the tape are acceptable, because the configuration of the tape and tubing will prevent the coiled cables from unwinding.

Figure 11:
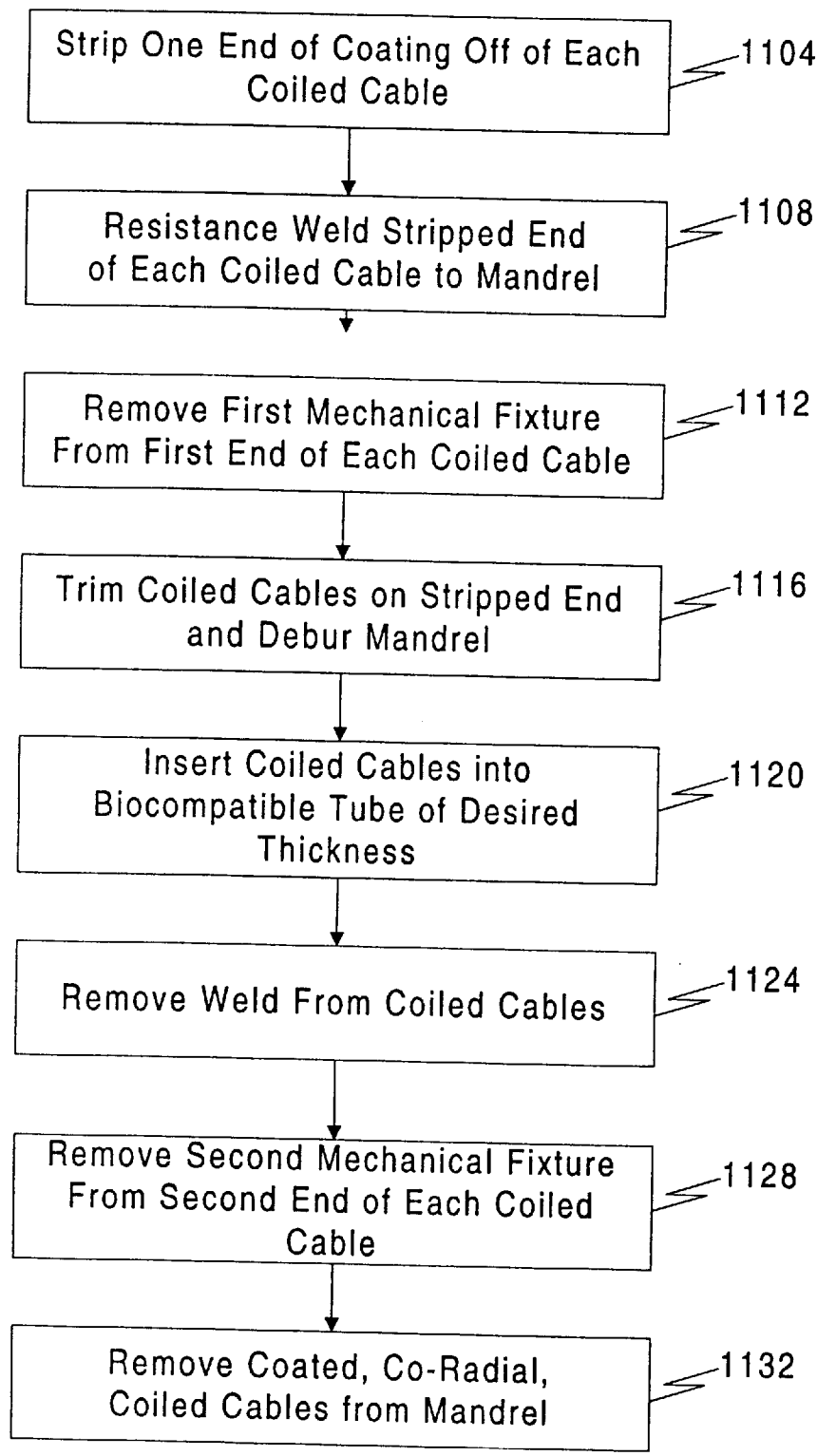
FIG. 11 is a flowchart showing a fifth embodiment for performing a second stage process for winding coiled cable structures according to the present invention.

FIG. 11 shows a fifth embodiment of second stage process step 640. In this process, the polymer coating near the first end of each of the cables is stripped, either mechanically, thermally or photo-ablatively, to prepare for welding of the cables to the underlying mandrel, as shown in a step 1104. In a step 1108, the stripped end of each cable is resistance welded to the mandrel. Resistance, laser or other welding processes can be used.

After the first end of each cable has been welded to the mandrel, the first mechanical end fixture is removed from the first end of each of the coiled cables, as shown in a step 1112. In a step 1116, the first end of each cable is trimmed, and the mandrel is deburred to avoid damage to tubing which may be subsequently placed over the coiled cables.

Because the welding process reduces the cross-sectional area of the end fixture at the point of the weld, the first end of the coiled cables can be slid into a biocompatible tube in a step 1120. In an alternate embodiment, both ends of the coiled cables could be stripped and welded to the mandrel so that the coiled cables could be slid into the tube from either direction. Additionally, the tube can be solvent expanded to facilitate sliding it over the coiled cables in this as well as other embodiments.

In a step 1124, the weld is then removed from the first end of the coiled cables, possibly by cutting the mandrel off at the point of the weld. In a step 1128, the second end fixture is removed from the second end of the coiled cables, and the coiled cables are ready to be used to manufacture an implantable lead. After the weld and end fixtures have been removed, the coiled cables can be removed from the mandrel, as shown in a step 1132.

Figure 12:
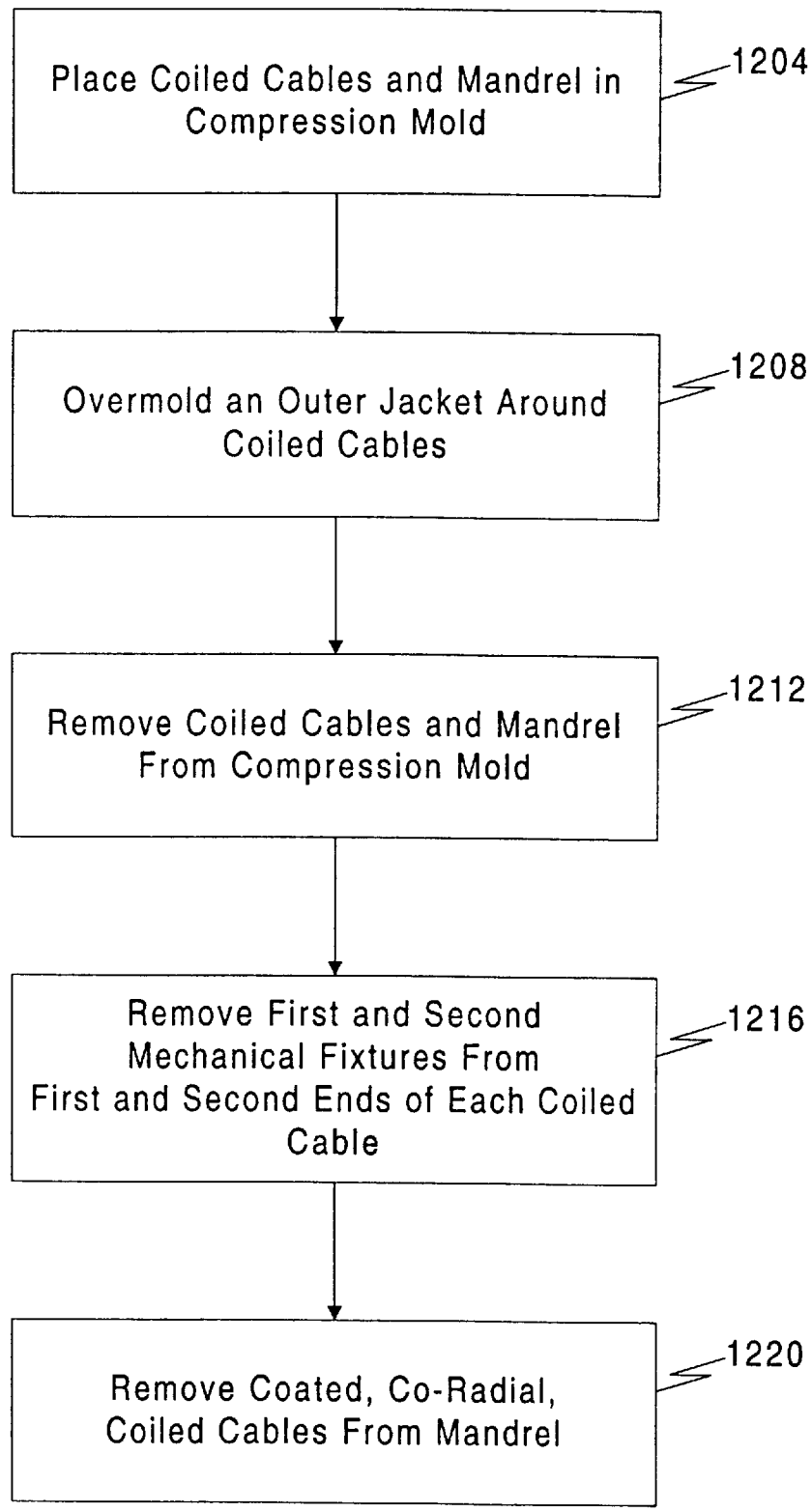
FIG. 12 is a flowchart showing a sixth embodiment for performing a second stage process for winding coiled cable structures according to the present invention.

FIG. 12 shows a sixth embodiment of second stage process step 640 of the present invention. In a step 1204, the cables and mandrel are placed in a compression mold. The compression mold is configured so that the end fixtures do not have to be removed prior to placing the cables and mandrel in the mold. The coiled cables are then overmolded with a biocompatible material, in a step 1208 to form an outer jacket around the coiled cables.

In molding a long conductor such as a lead, it may be difficult to create a perfectly concentric structure. Thus, different techniques should be used to optimize concentricity of the resulting tube, such as the use of force plates to prepack the mold, the use of a two stage molding processes, and the like. These techniques are well known to those skilled in the relevant art.

Once the outer jacket is molded over the coiled cable structure, the cables and mandrel are removed from the compression mold device in a step 1212. Then, the first and second end fixtures can be removed from the first and second ends of the coiled cables, as shown in a step 1216. The encased coiled cables may then be removed from the mandrel, in a step 1220, and are ready for use in the manufacture of implantable leads.

Figure 13:
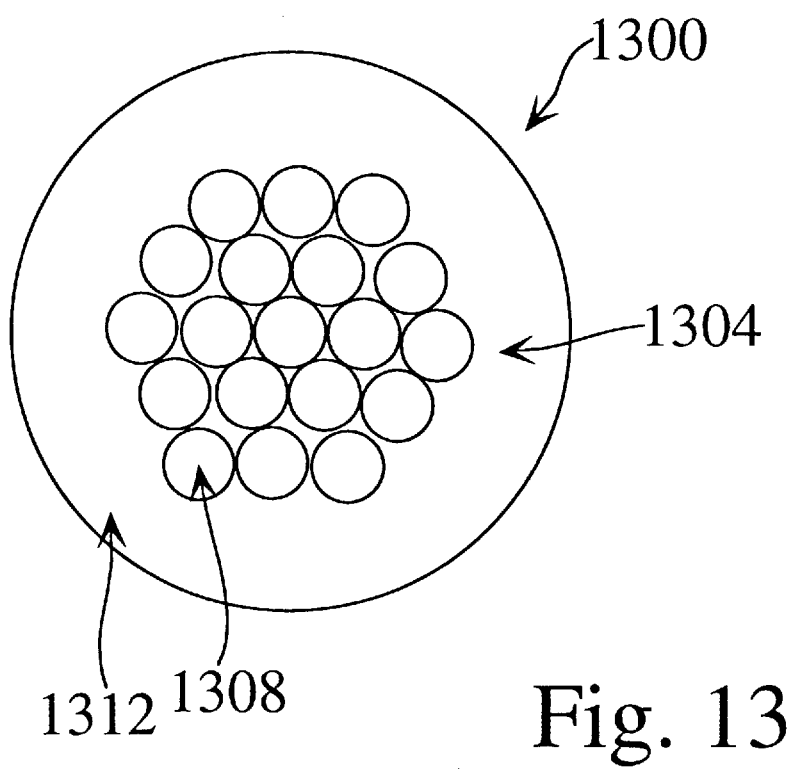
FIG. 13 shows a sectional view of a coated cable of the present invention.

FIG. 13 shows a sectional view of a 1×19 cable 1300 consisting of one strand 1304 formed of nineteen filaments 1308. Cable 1300 is coated with a thin fluoropolymer coating 1312. Cable 1300 is shown for example only. It would be apparent to one skilled in the relevant art that a variety of commonly known cable structures could be used in the present invention. For example, a second type of cable structure is shown in FIG. 14.

Figure 14:
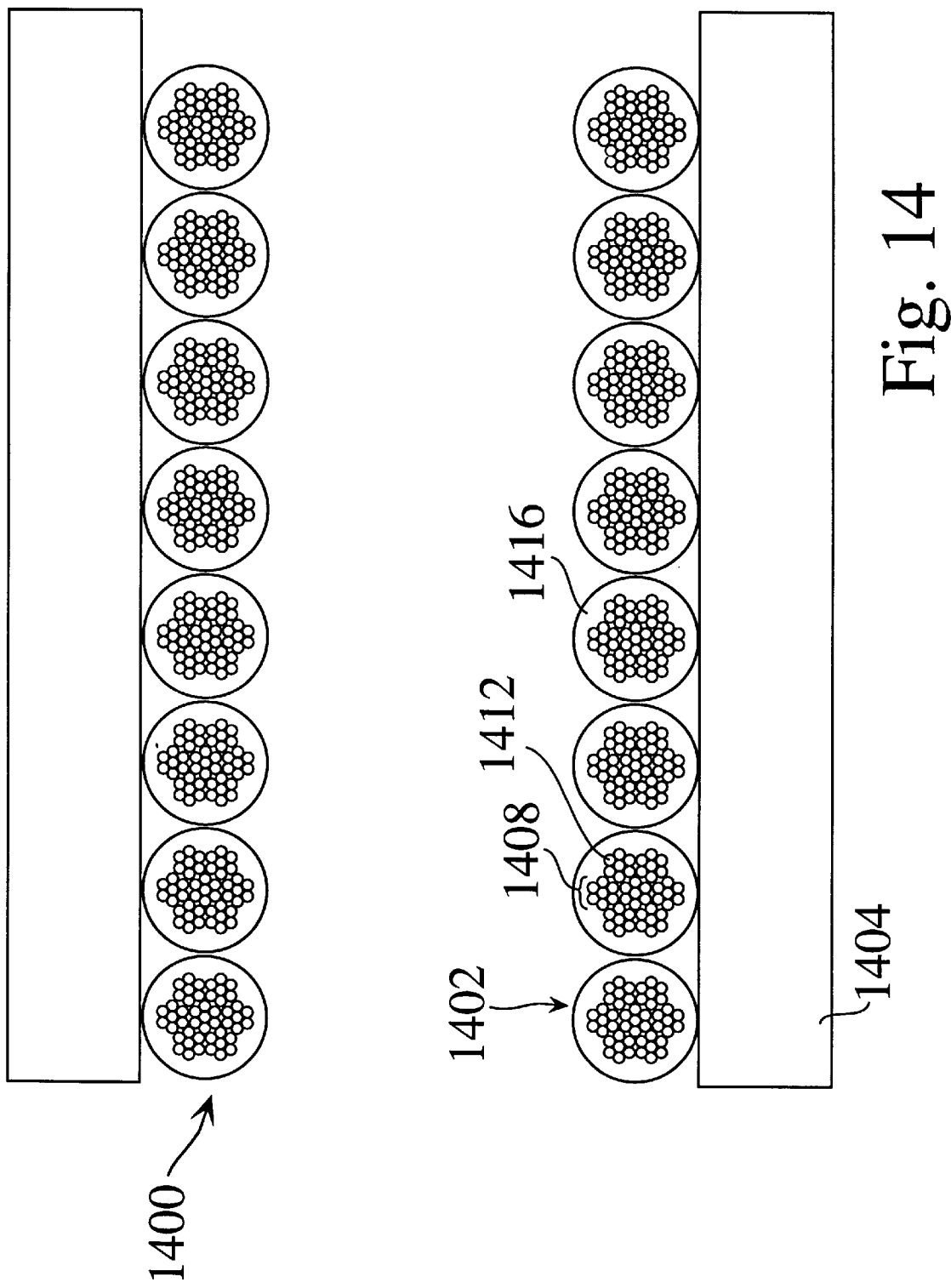
FIG. 14 shows a sectional view of a close-wound, coiled, co-radial cable of the present invention disposed in a silicone tube.

FIG. 14 shows a sectional view of a coil 1400 having a 7×7 coiled cable 1402 in a close wound formation, and inserted inside a silicone tube 1404. Coiled cable 1402 has seven strands 1408, each strand 1408 having seven small filaments 1412. Coiled cable 1402 is coated with a thin fluoropolymer coating 1416.

FIG. 15 shows a coil 1500 having a 1×19 cable 1502 in a space wound formation, and inserted inside a silicone tube 1504. Cable 1502 has one strand 1508 formed from a nineteen small filaments 1512. Cable 1502 is coated with a thin fluoropolymer coating 1514. Coiled cable 1502 is coated with a silicone dispersion coating 1516. Silicone tube 1504 covers silicone dispersion coating 1516 and cable 1502.

FIG. 16 shows the coiled cable structure of the present invention when used to build a defibrillation lead 1600 having a long coil electrode 1604. In this embodiment, a tube 1616 is shown disposed over a coiled cable 1612, that has been welded to a mandrel (not shown). A second tube 1608, having a defibrillation electrode 1620 already wound on to it, is disposed around coiled cable 1612. Coil electrode 1604 is electrically connected to a coiled cable via one or more wires (not shown) through silicone tube wall 1608 at the point where the tubes abut one another and are sealed off by a molding (not shown). This particular embodiment of electrical connection results in cable conductors which do not terminate once an electrical connection is made, but rather travel from end to end.

While the invention has been particularly shown and described with reference to preferred embodiments thereof, it will be understood by those skilled in the art that various changes in form and details may be made therein without departing from the spirit and scope of the invention. For example, second stage processing may include the sliding of tubular electrode structures and various lengths of tubing over the coiled cable structure. These different structures could be molded or bonded together before or after removal of the mandrel and end fixtures. These structures may be rigid metallic rings or flexible polymers.

What Is claimed is:

1. A method for making a coiled cable lead, comprising the steps of:

(a) attaching a first end of a cable, having an insulative coating layer, to a mandrel, wherein said cable comprises a plurality of cable strands;

(b) winding said cable around said mandrel to form a coiled cable having a first attached to said mandral;

(c) attaching a second end of said coiled cable to said mandrel;

(d) performing second stage processing on said coiled cable to prevent said coiled cable from unwinding when said coiled cable is removed from said mandrel; and (e) removing said coiled cable from said mandrel.

2. The method of claim 1, wherein said coiled cable is formed from a plurality of cables.

3. The method of claim 2, wherein said step (b) comprises winding said plurality of cables around said mandrel in a co-radial configuration.

4. The method of claim 1, wherein said step (d) comprises:

(i) dipping said coiled cable in uncured silicone rubber dispersed in a solvent until a layer of coating of sufficient thickness to resist residual stresses in said coiled cable is formed; and (ii) curing said silicone rubber.

5. The method of claim 4, wherein said step (i) and said step (ii) are performed in a vacuum.

6. The method of claim 4, wherein said step (d) further comprises:

(iii) applying a tubing over said coiled cable following said step of curing said silicone rubber.

7. The method of claim 1, wherein said step (d) comprises:

(i) placing said coiled cable and said mandrel into a compression mold, wherein said compression mold is configured to accommodate said first and second ends of said coiled cable; and (ii) molding an outerjacket of biocompatible material around said coiled cable to form a compression molded coiled cable.

8. The method of claim 7, wherein said step (d) further comprises:

(iii) applying a tubing over said compression molded, coiled cable.

9. The method of claim 1, wherein said step (d) comprises wrapping tape around said coiled cable to create a restraining hoop around said coiled cable and form a taped coiled cable.

10. The method of claim 9, wherein said step (d) further comprises:

(iii) applying a tubing over said taped, coiled cable.

11. The method of claim 9, wherein said tape is made from at least one of the following: polyurethane, expanded polytetrafluoroethylene, polyimide and polytetrafluoroethylene.

12. The method of claim 1, wherein said step (d) comprises wrapping thread around said coiled cable to create a restraining hoop around said coiled cable and form a wrapped coiled cable.

13. The method of claim 12, wherein said step (d) further comprises:

(iii) applying a tubing over said wrapped, coiled cable.

14. The method of claim 1, wherein said step (d) comprises:
    (i) stripping said insulative layer from near said first end of said coiled cable while said coiled cable is under tension;
    (ii) welding said first stripped portion near said first end of said coiled cable to said mandrel;
    (iii) detaching said first end of said coiled cable from said mandrel;
    (iv) trimming said first end of said coiled cable and deburring said mandrel, so that a cross-sectional area of said first end of said coiled cable is less than or equal to a cross-sectional area of said coiled cable; and
    (v) applying an insulating outer layer to said coiled cable via said first end.

15. The method of claim 1, further comprising:
    (f) heating said coiled cable prior to step (d) such that residual stresses in said insulative coating layer are reduced.

16. A co-radial, multi-filar, coiled cable conductor, made from a method comprising the steps of:
    (a) attaching a first end of a plurality of cables, each having an insulating coating, to a mandrel, wherein said cables each comprise a plurality of cable strands;
    (b) winding said cables around said mandrel to form coiled cables having first ends attached to said mandrel;
    (c) attaching a second end of each of said coiled cables to said mandrel;
    (d) performing second stage processing on said coiled cables to prevent said coiled cables from unwinding when said coiled cables are removed from said mandrel; and
    (e) removing said coiled cables from said mandrel.

17. The coiled cable conductor of claim 16, wherein each of said cable strands is made from a filament, wherein said filament is drawn brazed strand.

18. The coiled cable conductor of claim 16, wherein each of said cable strands is made from a filament, wherein said filament is drawn filled tubing.

19. The coiled cable conductor of claim 16, further comprising the step of:
    (f) heating said coiled cable prior to said step (d) such that residual stresses in said insulative layer of said coiled cable are reduced.

20. The coiled cable conductor of claim 16, wherein said cables are space wound around said mandrel in said step (b).

21. The coiled cable conductor of claim 16, wherein said cables are close wound around said mandrel in said step (b).

* * * * *